(12) United States Patent
Kouno et al.

(10) Patent No.: US 6,344,582 B1
(45) Date of Patent: Feb. 5, 2002

(54) PROCESS FOR PRODUCING A 2-ADAMANTYL (METH>ACRYLATE

(75) Inventors: Nobuharu Kouno, Kawanishi; Hiroaki Fujishima, Toyonaka, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/506,829

(22) Filed: Feb. 18, 2000

(30) Foreign Application Priority Data

Feb. 22, 1999 (JP) ............................................ 11-043465

(51) Int. Cl.⁷ ............................ C07C 69/52; C07C 67/48
(52) U.S. Cl. ........................ 560/220; 560/218; 528/482; 525/328.8; 430/270.1
(58) Field of Search ................................ 560/220, 218; 528/482; 525/328.8; 430/270.1

(56) References Cited

FOREIGN PATENT DOCUMENTS

| EP | 856773 | * | 8/1998 |
|----|--------|---|--------|
| EP | 0856773 A1 | | 8/1998 |
| JP | 09073173 A | | 3/1997 |
| JP | 10161313 A | | 6/1998 |
| JP | 10182552 A | | 7/1998 |
| JP | 2000229911 | * | 8/2000 |

OTHER PUBLICATIONS

Nozaki, Koji et al., Journal of Photopolymer Science and Technology, vol. 10, No. 4 (1997) pp. 545–550.
Zueva et al, "Adsorption of acrylates and methacrylates on active carbons", in Zh. Prikl. Khim. (Leningrad) (1979), 52(4), 849–853.*

* cited by examiner

*Primary Examiner*—Gary Geist
*Assistant Examiner*—Devesh Khare
(74) *Attorney, Agent, or Firm*—Birch, Stewart, Kolasch & Birch, LLP

(57) ABSTRACT

An efficient process for producing a high quality 2-adamantyl (meth)acrylate of the formula (I):

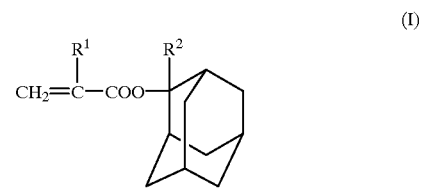

(I)

wherein $R^1$ is hydrogen or methyl and $R^2$ is hydrogen of lower alkyl, by using very common facilities and procedures, which reacting a (meth)acryloyl halide of the formula (II)

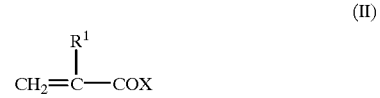

(II)

wherein $R^1$ is as defined above and X is halogen with a 2-adamantanol of the formula (III):

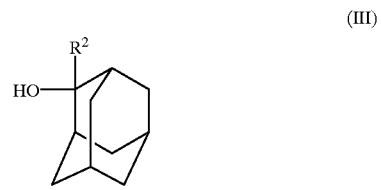

(III)

wherein $R^2$ is as defined above to form the 2-adamantyl (meth)acrylate of the formula (I), then treating a solution of this product in an organic solvent with active carbon, subsequently removing the active carbon, and thereafter separating a purified 2-adamantyl (meth)acrylate, is provided.

4 Claims, No Drawings

PROCESS FOR PRODUCING A 2-ADAMANTYL (METH)ACRYLATE

BACKGROUND OF THE INVENTION

The present invention relates to a process for producing a 2-adamantyl (meth)acrylate of the formula (I)

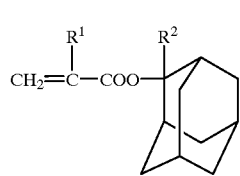

(I)

wherein $R^1$ is hydrogen or methyl and $R^2$ is hydrogen of lower alkyl.

JP-A-9-73173 discloses that the 2-adamantyl (meth)acrylate of the formula (I), especially a compound having alkyl as $R^2$, is useful as a raw material of chemical amplification resist. Such a 2-adamantyl (meth)acrylate is commonly produced by reacting a corresponding (meth)acryloyl halide and a corresponding 2-adamantanol. Since a product obtained by such a reaction contains much impurities and the crude product are often colored, purification treatment is generally conducted after the reaction. For example, when the above reaction is carried out in an organic solvent, the resulting reaction mixture is generally subjected to a post-treatment such as washing with water, the solvent is generally evaporated off, and column purification or distillation is generally conducted.

Further, a method wherein a (meth)acryloyl halide and a 2-adamantanone, both of which correspond to the above formula (I), are reacted has also been known. JP-A-10-182552 discloses a method wherein the reaction of the acid halide and the ketone is carried out in the presence of a specific Grignard reagent or organolithium compound. In such a reaction of the acid halide and the ketone, a product contains much impurities. Therefore, in the Examples in the publication, after the reaction is conducted in an organic solvent, the crude product obtained by concentration is subjected to column purification.

However, the column purification is not always efficient from a treatment capacity consideration. For example, the column purification using a silica gel column requires a large amount of silica gel (packing) as much as about 30 times by weight with respect to a substrate to be purified, and it takes much time to pass a solution to be purified through the column. In addition, purification by distillation require special conditions such as addition of stabilizers and high vacuum because of insufficient thermal stability of the 2-adamantyl (meth)acrylate to be purified. Therefore, it is difficult to apply column purification and distillation particularly for the purification of the above 2-adamantyl (meth)acrylate in an industrial scale. Further, it is also difficult to carry out the aforementioned method disclosed in JP-A-10-182552 in an industrial scale because the Grignard reagent or organolithium compound is expensive or requires careful handling and column purification is also necessary.

The present inventors have studied intensively to produce a purified product of the 2-adamantyl (meth)acrylate of the formula (I) by a method which can be carried out easily even in an industrial scale. As a result, they have found that a 2-adamantyl (meth)acrylate of high quality can be produced very efficiently by adsorbing and removing impurities formed in the reaction of a (meth)acryloyl halide and a 2-adamantanol with active carbon. The present invention was thus accomplished.

SUMMARY OF THE INVENTION

The present invention provides a process for producing a 2-adamantyl (meth)acrylate of the formula (I):

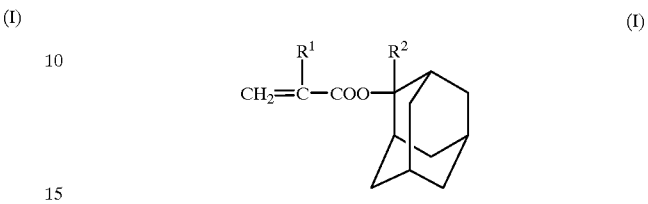

(I)

wherein $R^1$ is hydrogen or methyl and $R^2$ is hydrogen of lower alkyl, which comprises reacting a (meth)acryloyl halide of the formula (II):

(II)

wherein $R^1$ is as defined above and X is halogen with a 2-adamantanol of the formula (III):

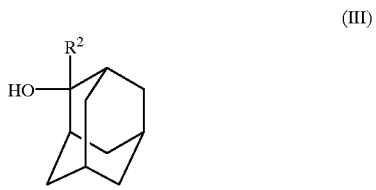

(III)

wherein $R^2$ is as defined above to form the 2-adamantyl (meth)acrylate of the formula (I), then treating a solution of this product in an organic solvent with active carbon, subsequently removing the active carbon, and thereafter separating a purified 2-adamantyl (meth)acrylate.

PREFERRED EMBODIMENT OF THE INVENTION

In the formula (II) representing the (meth)acryloyl halide, a raw material, the halogen represented by X may be, for example, chlorine and bromine. Specific examples of such a (meth)acryloyl halide include acryloyl chloride, methacryloyl chloride, acryloyl bromide and methacryloyl bromide. In the formula (III) representing the 2-adamantanol, another raw material, the lower alkyl represented by $R^2$ may, for example, have from 1 to 4 carbon atoms. Specific examples of such a 2-adamantanol include 2-adamantanol, 2-methyl-2-adamantanol and 2-ethyl-2-adamantanol.

In the process of the present inventin, the condensation reaction of the (meth)acryloyl halide of the formula (II) with the 2-adamantanol of the formula (III) to produce the 2-adamantyl (meth)acrylate of the formula (I) can be conducted in accordance with known methods. For example, the (meth)acryloyl halide of the formula (II) and the 2-adamantanol of the formula (III) may be reacted in an appropriate solvent. As a solvent used in this reaction, organic polar solvents are advantageous. Examples thereof include ketones such as acetone, methyl ethyl ketone and methyl isobutyl ketone, and ethers such as tetrahydrofuran and tert-butyl methyl ether. Amount of the solvent preferably ranges approximately from 1 to 10 times by weight with respect to the total amount of the (meth)acryloyl halide of the formula (II) and the 2-adamantanol of the formula (III). An amount as much as approximately from 1 to 5 times by weight is more preferably from considerations of volume efficiency and the like.

In this reaction, it is advantageous that the reaction is carried out in the presence of a dehydrohalogenating agent because a hydrogen halide is formed by condensation. Examples of the dehydrohalogenating agent usable in the above case include amines such as triethylamine and pyridine, and inorganic bases such as sodium carbonate and potassium carbonate. In particular, an organic amine is preferable. When a dehydrohalogenating agent is used, for example, following methods can be adopted:

a method wherein the 2-adamantanol of the formula (III) and the dehydrohalogenating agent are added in an adequate solvent and, then, the (meth)acryloyl halide of the formula (II) are gradually added thereto; and a method wherein the (meth)acryloyl halide of the formula (II) and the 2-adamantanol of the formula (III) are dissolved in an adequate solvent and the dehydrohalogenating agent is gradually added thereto, and the like. When the dehydrohalogenating agent is used, the amount thereof is generally approximately from 1 to 5 times by mol, preferably approximately from 1 to 3 times by mol with respect the 2-adamantanol of the formula (III).

In this reaction, a molar ratio of the (meth)acryloyl halide of the formula (II) to the 2-adamantanol of the formula (III) is important to make the reaction proceed smoothly. In general, it is desirable that the (meth)acryloyl halide of the formula (II) is used in a ratio of from about 1 to about 3 mol per mol of the 2-adamantanol of the formula (III), although preferably molar ratio varies depending upon the type of the dehydrohalogenating agent. When an organic amine is used as the dehydrohalogenating agent, the (meth)acryloyl halide of the formula (II) is preferably as much as approximately from 1.1 to 2.5 times by mol with respect to the 2-adamantanol of the formula (III). When an inorganic base is used as the dehydrohalogenating agent, the (meth)acryloyl halide is preferably as much as approximately from 2 to 3 times by mol with respect to the 2-adamantanol.

This reaction can proceed at any temperature between a low temperature of about -10° C. to a high temperature of about the boiling point of the reaction solvent. However, it is economical to conduct the reaction at temperatures ranging from about 40° C. to the boiling point of the reaction solvent from an aspect of progress of the reaction. Further, the reaction can be conducted under atmospheric pressure, and the reaction time is approximately from 2 to 30 hours.

When the condensation reaction has completed, the surplus unreacted (meth)acryloyl halide is converted into an ester and deactivated by addition of alcohol, if necessary. Further, washing with water and/or an aqueous sodium chloride solution is conducted, if necessary. Thereafter, the treatment with active carbon is conducted according to the present invention. The active carbon treatment may be conducted in a state where the product is dissolved in the reaction solvent. For example, the condensation reaction was conducted in a polar solvent, and then the resulting solution of the product containing the polar reaction solvent is treated with active carbon.

In addition, under some conditions in the condensation reaction, an appreciable amount of polymeric components are formed as by-products. In such cases, if the product is dissolved in the reaction solvent which is a polar solvent, the polymeric impurities sometimes can not be removed sufficiently.

In such a case, the polymeric impurities can be removed efficiently and the 2-adamantyl (meth)acrylate of the formula (I) can be obtained in high purity by once removing the polar reaction solvent from the reaction mixture by such a method as concentration evaporation, dissolving the resulting crude product in a nonpolar solvent and subjecting the resulting solution of the crude product in the nonpolar solvent to an active carbon treatment. The nonpolar solvent used here may be any hydrocarbon solvent with no polarity. Specific examples thereof include aliphatic hydrocarbon solvents such as hexane and heptane. The nonpolar solvent is used in an amount of approximately from 0.5 to 10 times by weight, preferably approximately from 1 to 5 times by weight with respect to the 2-adamantyl (meth)acrylate.

Alternatively, it is also effective to conduct the active carbon treatment in two steps in which active carbon treatment is conducted in a state where the product is dissolved in the polar reaction solvent and then active carbon treatment is conducted again in a state where the product is dissolved in a nonpolar solvent. For example, such a two-step active carbon treatment can be conducted according to the following successive processes:

1) the reaction mixture, in which the desired compound is dissolved in the reaction solvent, is treated with active carbon, 2) the active carbon is removed;

3) the reaction solvent is removed from the resulting solution by concentration evaporation or the like to obtain a crude product;

4) the crude product is dissolved in a nonpolar solvent; and then 5) the solution is treated with active carbon again.

In general, the active carbon treatment may be conducted in such a manner that active carbon is added to a solution in which the desired 2-adamantyl (meth)acrylate, is dissolved in the reaction solvent or a non-polar solvent and then the mixture is stirred so that the solution and the active carbon can contact well. The treatment time is approximately from 5 minutes to 1 hour, in general. The type of the active carbon to be used is not particularly restricted as long as it has absorbability. Amount of the active carbon is preferably within the range of approximately from 0.05 to 1 time by weight, more preferably approximately 0.1 to 0.7 time by weight with respect to the desired 2-adamantyl (meth)acrylate.

After the treatment with active carbon, the used active carbon, which remains as a solid, needs to be removed. The removal of the active carbon can be performed by passing the solution, in which the active carbon is suspended, through a conventional filter. Under some conditions in the condensation reaction, monomeric impurities such as the unreacted 2-adamantanol of the formula (III) may be present in appreciable amounts. Such monomeric impurities sometimes can not be removed sufficiently only by normal filtration. In such a case, precoating the filter with silica gel is effective when the filtration is conducted. Precoating can be carried out, for example, by the following methods:

1) a method which comprises spreading silica gel powder all over the filter and thereafter pouring an adequate solvent, for example a solvent constituting the solution to be treated such as hexane and heptane, to make the silica gel adhere; and 2) a method which comprises dispersing silica gel in an adequate solvent and thereafter pouring the resulting dispersion onto the filter to make the silica gel adhere. In such cases of precoating with silica gel, silica gel may be used in an amount ranging approximately from 0.05 to 1 time by weight with respect to the 2-adamantyl (meth)acrylate to be purified. A preferred amount of silica gel for precoating is approximately from 0.1 to 0.7 time by weight with respect to the 2-adamantyl (meth)acrylate.

As mentioned above, silica gel is often used for column purification. In such a case, silica gel as much as about 30 times by weight respect to the substrate to be purified (the 2-adamantyl (meth)acrylate in this invention) is required. However in a case where a solution after treatment with active carbon is treated, silica gel may be used in an amount much less than that used in column purification.

As mentioned above, the 2-adamantyl (meth)acrylate represented by the formula (I) of high quality can be isolated by conducting the active carbon treatment and thereafter subjecting the solution after removal of the active carbon to adequate post-treatment such as concentration.

EXAMPLES

The present invention is further explained in detail by way of the following Examples, but the invention is not limited thereto. In the Examples, % indicating concentration is by weight unless otherwise indicated. In addition, in the following Examples, control of reactions was carried out using gas chromatography. Formation of the final objectives were ascertained by proton nuclear magnetic resonance (NMR), gas chromatograph and gel permeation chromatography (GPC).

EXAMPLE 1

Into a reaction vessel were charged 2.1 liters of methyl isobutyl ketone, 665.2 g (4.0 mol) of 2-methyl-2-adamantanol and 607.29 g (6.0 mol) of triethylamine, and their temperature was elevated to 60° C. under stirring. To the mixture, a solution prepared by dissolving 434.55 g (4.8 mol) of acryloyl chloride in 0.4 liter of methyl isobutyl ketone was added dropwise. At the end of the dropwise addition, the temperature was reached about 80° C. with the reaction heat. The mixture was kept at 80° C. for 2 hours with stirring to complete the reaction. After cooling, 64.02 g (2.0 mol) of methanol was added dropwise to deactivate the unreacted acryloyl chloride while keeping the temperature below 40° C. Then, 3.3 liters of water was added thereto to wash the mixture, followed by separation of the mixture into layers. Thereafter, 2.8 liters of a saturated aqueous sodium chloride solution was added to the organic layer to wash it again, and the mixture was separated into layers. To the organic layer after separation was added 204 g of active carbon "Carborafin" manufactured by Takeda Chemical Industries, Ltd. and stirred for 1 hour. The mixture was filtered thereafter and the residue was washed with 2 liters of methyl isobutyl ketone. The filtrate and the washing effluents were combined and concentrated at a bath temperature of 45° C. to obtain 886.17 g of crude 2-methyl-2-adamantyl acrylate.

To 886.17 of the crude 2-methyl-2-adamantyl acrylate were added 1,635 g of hexane and 204 g of active carbon (Carborafin) and the resulting mixture was stirred for 1 hour. Then, the mixture was filtered through a filter precoated with 204 g of silica gel and the residue was washed with 3 liters of hexane. The filtrate and washing effluents were combined and concentrated at a bath temperature of 45° C. to yield 832.37 g of pure 2-methyl-2-adamantyl acrylate as a slightly yellowish transparent liquid. The yield was 94% based on the charged 2-methyl-2-adamantanol. NMR pattern of this compound coincided with that of its column-purified sample. This compound had 99% purity determined by internal standard gas chromatography, 96% area percentage purity determined by GPC detected by using ultraviolet ray (UV), and 97% GPC area percentage purity detected by using differential refractive index (RI).

EXAMPLE 2

Into a reaction vessel were charges 33.26 g of methyl ethyl ketone, 16.63 g (0.1 mol) of 2-methyl-2-adamantanol and 30.36 (0.3 mol) of triethylamine, and their temperature was elevated to 60° C. under stirring. To the mixture, a solution prepared by dissolving 13.58 g (0.15 mol) of acryloyl chloride in 16.63 g of methyl ethyl ketone was added dropwise. At the end of dropwise addition, the temperature was reached 77° C. and the mixture was boiling with the reaction heat. The mixture was kept in a boiling state for 3 hours with stirring to complete the reaction. After cooling, 3.20 g (0.1 mol) of methanol was added dropwise to deactivate the unreacted acryloly chloride while keeping the temperature below 40° C. Then, 103 g of water was added to wash the mixture and thereafter the mixture was separated into layers. To the brown organic layer, 10 g of active carbon (Carborafin) was added and stirred. The mixture was thereafter filtered and the residue was washed with methyl ethyl ketone. The filtrate and washing effluents were combined and concentrated at a bath temperature of 45° C. to obtain 21.68 g of reddish orange crude 2-methyl-2-adamantyl acrylate.

To 10 g of the crude 2-methyl-2-adamantyl acrylate was added 10 g of hexane and 5 g of active carbon (Carborafin) and the resulting mixture was stirred for 1 hour. Then, the mixture was filtered and the residue was washed with hexane. The filtrate and washing effluents were combined and concentrated at a bath temperature of 45° C. to yield 9.25 g of pure 2-methyl-2-adamantyl acrylate as a slight yellow transparent liquid. The yield was 98% based on the charged 2-methyl-2-adamantanol. NMR pattern of this compound was about the same as that of its column-purified sample. This compound had 100% purity determined by internal standard gas chromatography, 89% GPC area percentage purity detected by using UV, and 93% GPC area percentage purity detected by using RI.

EXAMPLE 3

To 10 g of the crude 2-methyl-2-adamantyl acrylate obtained in the first half of Example 2 were added 10 g of hexane and 5 g of active carbon (Carborafin) and the resulting mixture was stirred for 1 hour. The mixture was filtered through a filter precoated with 5 g of silica gel to yield 8.75 g of pure 2-methyl-2-adamantyl acrylate as an approximately colorless transparent liquid. The yield was 93% based on the charged 2-methyl-2-adamantanol. NMR pattern of this compound coincided with that of its column-purified sample. This compound had 100% purity determined by internal standard gas chromatography, 98% GPC area percentage purity detected by using UV, and 95% GPC area percentage purity detected by using RI.

A comparison of the results of Example 3 to those of Example 2 has revealed that precoating a filter with silica gel removes a slight amount of impurities and also improves hue of the product.

EXAMPLE 4

Into a reaction vessel were charged 598.54 g of methyl isobutyl ketone and 74.82 g (0.45 mol) of 2-methyl-2- adamantanol, and 72.75 g (0.675 mol) of methacryloyl chloride was poured thereto at room temperature under stirring. To the mixture, 82.79 g (0.81 mol) of triethylamine was added dropwise and the resulting mixture was left as it was for 15 minutes. The mixture was heated up to 80° C. and kept at this temperature for 24 hours under stirring. After cooling, 14.42 g (0.45 mol) of methanol added dropwise to deactivate the unreacted methacryloyl chloride while keeping the temperature below 10° C. Then, 223 g of water was added to wash the mixture and thereafter the mixture was separated into layers. To the organic layer, 112 g of a saturated aqueous sodium chloride solution was added, the resulting mixture was neutralized with a 5% aqueous sulfuric acid solution so as to adjust pH to from 7 to 8. Thereafter, the mixture was separated into layers. The organic layer after separation was concentrated at a bath temperature of 40° C. to yield 109.93 g of brown crude 2-methyl-2-adamantyl methacrylate.

This crude product was dissolved in 316 g of hexane, and 21 g of active carbon (Carborafin) was added thereto. The resulting mixture was stirred for 1 hour. Then, the mixture was filtered through a filter precoated with 21 g of silica gel and the residue was washed with hexane. The filtrate and washing effluents were combined and concentrated at a bath temperature of 45° C. to yield 99.36 g of pure 2methyl-2-adamantyl methacrylate as a colorless transparent liquid. The yield was 94% based on the charged 2-methyl-2-adamantanol. NMR pattern of this compound was about the same as that of its column-purified sample. This compound had 93% purity determined by internal standard gas chromatography, 86% GPC area percentage purity detected by using UV, and 94% GPC area percentage purity detected by using RI.

EXAMPLE 5

Into a reaction vessel were charged 116.41 g of tetrahydrofuran and 16.63 g (0.1 mol) of 2-methyl-2-adamantanol, and 21.56 g (0.2 mol) of methacryloyl chloride was poured thereto at -10° C. under stirring. To the mixture, 25.56 g (0.25 mol) of triethylamine was added dropwise and the resulting mixture was left as it was for 15 minutes. The mixture was heated up to 69° C., the refluxing temperature, and stirring was continued for 11 hours while maintaining the refluxing state to react the mixture. After cooling, 6.41 g (0.2 mol) of methanol was added dropwise at -10° C. to deactivate the unreacted methacryloyl chloride. Then, the mixture was diluted with 116.41 g of methy isobutyl ketone. To the mixture, 68.87 g of water was added to wash it and thereafter the mixture was separated into layers. To the organic layer was added 112 g of a saturated aqueous sodium chloride solution. The resulting mixture was neutralized, under ice cooling, with a 5% aqueous sulfuric acid solution so as to adjust pH to from 7 to 8 and thereafter the mixture was separated into layers. The organic layer after separation was concentrated at a bath temperature of 40° C. to yield 23.62 g of brown crude 2-methyl-2-adamantyl methacrylate.

This crude product was dissolved in 70.32 g of hexane, and 11.72 g of active carbon (Carborafin) was added thereto and the resulting mixture was stirred for 1 hour. The mixture was filtered through a filter precoated with 11.72 g of silica gel and the residue was washed with hexane. The filtrate and washing effluents were combined and concentrated at a bath temperature of 40° C. to yield 19.77 g of pure 2-methyl-2-adamantyl methacrylate as a slightly yellowish transparent liquid. The yield was 84% based on the charged 2-methyl-2-adamantanol. NMR pattern of this compound was about the same as that of its column-purified sample. This compound had 98% purity determined by internal standard gas chromatography, 96% GPC area percentage purity detected by using UV, and 99% GPC area percentage purity detected by using RI.

Each of the 2-methyl-2-adamantyl acrylate or 2-methyl-2-adamantyl methacrylate obtained in the Examples was ascertained not to be significantly different when used as a raw material of resin for chemical amplification resist from the column-purified samples obtained according to a conventional method.

The present invention can produce 2-adamantyl (meth) acrylates of high quality more efficiently by using very common facilities and procedures in comparison with conventional methods such as column purification and distillation.

What is claimed is:

1. A process for producing a 2-adamantyl (meth) acrylate of the formula (I):

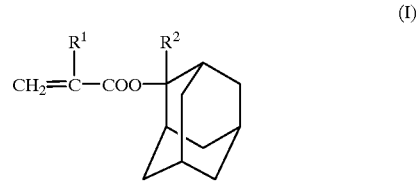

(I)

wherein R1 is hydrogen or methyl and R2 is hydrogen of lower alkyl, which comprises reacting a (meth)acryloyl halide of the formula (II)

(II)

wherein R1 is as defined above and X is halogen with a 2-adamantanol of the formula (III):

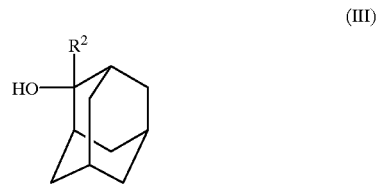

(III)

wherein R2 is as defined above to form the 2-adamantyl (meth)acrylate of the formula (I) in a polar solvent, and then conducting the following steps (1)–(4) in sequence:
 (1) removing the solvent used in the reaction to obtain a crude product, which is then dissolved in a nonpolar organic solvent,
 (2) treating the solution of this product in the nonpolar organic solvent with active carbon, wherein polymeric impurities are adsorbed on said active carbon,
 (3) removing the active carbon, and
 (4) separating a purified 2-adamantyl (meth) acrylate.

2. The process according to claim 1 which comprises reacting the (meth)acryloyl halide of the formula (II) with the 2-adamantanol of the formula (III) in a polar solvent, treating, with active carbon, a solution of the reaction product in an organic solvent which contains the polar solvent used in the reaction, and, thereafter, further treating, with active carbon, a solution of this product in a nonpolar organic solvent produced by removing the active carbon used firstly and the polar solvent to obtain a crude product which is then dissolved in a nonpolar organic solvent.

3. The process according to claim 2, wherein the nonpolar organic solvent is an aliphatic hydrocarbon solvent.

4. The process according to claim 1, wherein removing the active carbon is conducted with filtration using a filter precoated with silica gel.

* * * * *